United States Patent
Spahr et al.

(10) Patent No.: US 10,052,483 B2
(45) Date of Patent: Aug. 21, 2018

(54) COCHLEAR IMPLANT APPARATUS, SYSTEMS AND METHODS WITH AUTOMATIC CONTRALATERAL SIGNAL ROUTING

(71) Applicant: Advanced Bionics AG, Staefa (CH)

(72) Inventors: Anthony J. Spahr, Newhall, CA (US); Erin E. Castioni, Ventura, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/518,407

(22) PCT Filed: Oct. 28, 2014

(86) PCT No.: PCT/US2014/062738
§ 371 (c)(1),
(2) Date: Apr. 11, 2017

(87) PCT Pub. No.: WO2016/068891
PCT Pub. Date: May 6, 2016

(65) Prior Publication Data
US 2017/0312511 A1 Nov. 2, 2017

(51) Int. Cl.
*A61N 1/36* (2006.01)
*A61N 1/372* (2006.01)

(52) U.S. Cl.
CPC ....... *A61N 1/3606* (2013.01); *A61N 1/36038* (2017.08); *A61N 1/37252* (2013.01)

(58) Field of Classification Search
CPC .. A61N 1/36; A61N 1/36036; A61N 1/36038; A61N 1/3606; A61N 1/37211; A61N 1/3722
See application file for complete search history.

(56) References Cited

U.S. PATENT DOCUMENTS

| | | | |
|---|---|---|---|
| 5,824,022 A | 10/1998 | Zilberman et al. | |
| 8,027,495 B2 | 9/2011 | Roeck | |
| 8,700,169 B1 | 4/2014 | Chapa et al. | |
| 2011/0125218 A1* | 5/2011 | Busby | A61N 1/36032 607/57 |
| 2012/0053656 A1 | 3/2012 | Chapa et al. | |
| 2012/0232616 A1* | 9/2012 | Van Baelen | A61N 1/36032 607/57 |
| 2013/0301860 A1 | 11/2013 | Neumeyer et al. | |
| 2014/0188189 A1* | 7/2014 | Mishra | A61N 1/36032 607/57 |

(Continued)

FOREIGN PATENT DOCUMENTS

| | | |
|---|---|---|
| EP | 1320281 B1 | 8/2013 |
| WO | WO 2013/101088 A1 | 7/2013 |

OTHER PUBLICATIONS

PCT International Search and Written Opinion dated Jun. 9, 2015 for PCT App. Ser. No. PCT/US2014/062738.
Phonak Insight "Binaural Directionality," Jul. 2010.

*Primary Examiner* — Allen Porter, Jr.
(74) *Attorney, Agent, or Firm* — Henricks Slavin LLP

(57) ABSTRACT

A cochlear implant sound processor including processor apparatus that, in response to being paired with a cochlear implant, converts audio signals from a microphone into stimulation data and transfer the stimulation data to cochlear implant, and in response to a failure to detect the cochlear implant, transfers the audio signals to a contralateral sound processor. Systems and methods are also disclosed.

12 Claims, 4 Drawing Sheets

(56) References Cited

U.S. PATENT DOCUMENTS

2014/0330344 A1* 11/2014 Mishra ............... A61N 1/36032
607/57
2016/0136425 A1* 5/2016 Hamacher ............ H04R 25/407
607/57

\* cited by examiner

COCHLEAR IMPLANT APPARATUS, SYSTEMS AND METHODS WITH AUTOMATIC CONTRALATERAL SIGNAL ROUTING

CROSS-REFERENCE TO RELATED APPLICATIONS

This application is the U.S. National Stage of PCT App. Ser. No. PCT/US2014/062738, filed Oct. 28, 2014.

BACKGROUND

1. Field

The present disclosure relates generally to implantable cochlear stimulation ("ICS") systems.

2. Description of the Related Art

ICS systems are used to help the profoundly deaf perceive a sensation of sound by directly exciting the auditory nerve with controlled impulses of electrical current. Ambient sound pressure waves are picked up by an externally worn microphone and converted to electrical signals. The electrical signals, in turn, are processed by processor apparatus, converted to stimulation data (e.g., a pulse sequence having varying pulse widths and/or amplitudes), and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. Alternatively, the implantable electrode array may be directly inserted into the cochlear nerve without residing in the cochlea.

Conventional ICS systems commonly include an implantable device (or "cochlear implant") and an external sound processor with a housing, processor apparatus, a microphone that is in communication with the processor apparatus, and a battery or is other power supply. In some instances, the sound processor is worn behind the ear (a "BTE sound processor") and includes an earhook. The sound processor transmits stimulation data, as well as power from its power supply, to the implantable device by way of an inductive link. To that end, ICS systems include a headpiece that is connected to the sound processor by a cable. The headpiece has a coil antenna that is used to connect the headpiece (and BTE sound processor by way of the headpiece) to the implantable device via an inductive link. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

Some ICS systems, which are known as electro-acoustic stimulation ("EAS") systems, also include a receiver (or "speaker"). Such systems provide cochlear implant and hearing aid functionality to the same ear. The receiver delivers amplified low frequency sound pressure waves to the ear canal, the cochlear implant delivers high frequency information through electrical stimulation, and the auditory nerve combines the acoustic and electrical stimuli into one auditory signal.

Many cochlear implant users receive a unilateral implantation, i.e. a single cochlear implant for one ear, as well as a pair of sound processors. One sound processor is carried on (or otherwise associated with) the ear that received the implant (the "implanted ear"). Ipsilateral sounds, i.e., sounds that are picked up by the microphone(s) of the sound processor worn on the same side of the body as the cochlear implant, are converted into stimulation signals by the sound processor and transferred to the cochlear implant. The other sound processor is kept in storage and used as a backup sound processor.

SUMMARY

The present inventors have determined that conventional ICS systems, including EAS systems, are susceptible to improvement. For example, the present inventors have determined that the backup sound processor that is provided to a unilateral implantation patient could have utility beyond simply being a backup. In particular, the present inventors have determined that the backup sound processor could be carried on the contralateral non-implanted ear (or another contralateral location on the body) and used to pick up sound on the contralateral side. The sound processor on the contralateral side may then transmit sound signals to the sound processor associated with the implanted ear. The stimulation data transmitted to the cochlear implant may then be based on both ipsilateral sound and contralateral sound.

A method of operating a sound processor in accordance with one of the present inventions includes determining, with the sound processor, whether the sound processor is paired with a cochlear implant. In response to a determination that the sound processor is paired with the cochlear implant, the sound processor operates in a first mode where the sound processor communicates with the cochlear implant, and in response to a determination that the sound processor is not paired with the cochlear implant, the sound processor operates in a second mode, that is different than the first mode, where the sound processor transmits audio signals to a contralateral sound processor and does not communicate with the cochlear implant.

A sound processor in accordance with one of the present inventions includes a transmitter configured to transmit audio signals to a contralateral sound processor, and processor apparatus operable in a first mode, in response to a detection of the cochlear implant, to convert audio signals from a microphone into stimulation data and to transfer the stimulation data to the headpiece, and operable in a second mode, in response to a failure to detect the cochlear implant, to transfer the audio signals to a contralateral sound processor with the transmitter.

A system in accordance with one of the present inventions includes a single cochlear implant, a first sound processor with a first microphone, and a second sound processor with a second microphone. The first sound processor is configured to determine whether or not it is paired with the single cochlear implant, to convert audio signals from the first microphone into stimulation data in response to being paired with the single cochlear implant, and to transfer the audio signals from the first microphone to the second sound processor in response to not being paired with the single cochlear implant. The second sound processor is configured to determine whether or not it is paired with the single cochlear implant, to convert audio signals from the second microphone into stimulation data in response to being paired with the single cochlear implant, and to transfer the audio signals from the second microphone to the first sound processor in response to not being paired with the single cochlear implant.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of systems that provide sound (i.e., either sound or a perception of sound) to the hearing impaired as well as others who require such systems on a situational basis. One example of such a system is an ICS system where an external sound processor communicates with a cochlear implant and, accordingly, the present inventions are discussed in the context of ICS systems. The present inventions are not, however, limited to the ICS systems illustrated and described herein and may be used in combination with other ICS systems that currently exist, or are yet to be developed.

Figure 1:
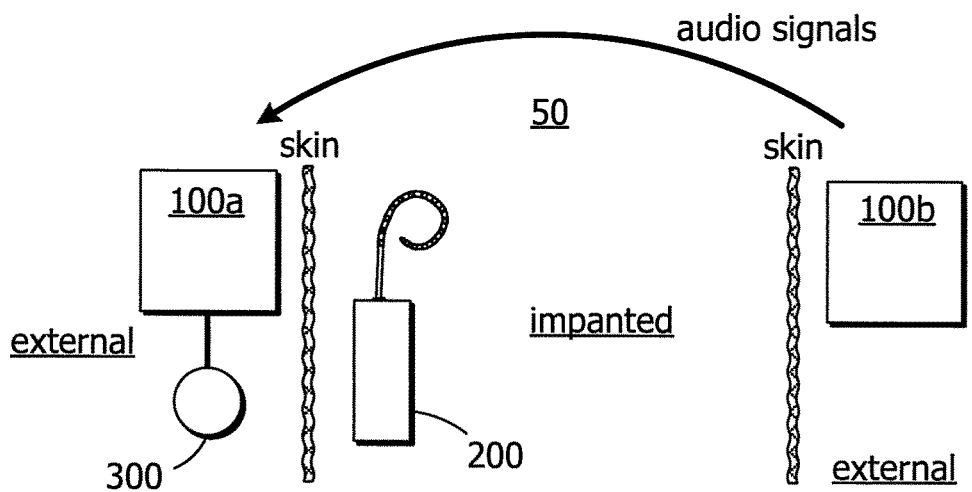
FIG. 1 is a block diagram of an ICS system in accordance with one embodiment of a present invention.

One example of an ICS system is the system generally represented by reference numeral 50 in FIG. 1. The exemplary ICS system 50 includes a pair of BTE sound processors 100a and 100b, a single implantable cochlear simulator 200 (or "cochlear implant"), and a headpiece 300. As used herein, "single" means "one and no more than one" and, accordingly, there is an implanted ear that is associated with the cochlear stimulator 200 and a non-implanted ear that is not associated with a cochlear stimulator. The use of a single cochlear implant is sometimes referred to as a unilateral implantation. The sound processors 100a and 100b are identical to one another in the illustrated embodiment and are each configured to operate in at least a first mode when associated with the implanted ear and a second mode, which is different than the first mode, when associated with the non-implanted ear. Briefly, the sound processor that is worn on the implanted ear (here, sound processor 100a) operates in the first mode and converts electrical signals from one or more microphones into stimulation data. The stimulation data and, in many instances power, is supplied to the headpiece 300. The headpiece 300 transmits the stimulation data, and in many instances power, to the cochlear stimulator 200 by way of a wireless link. The other sound processor (here, sound processor 100b) is worn on the non-implanted ear and is not paired with the cochlear stimulator 200. Instead of transmitting stimulation data to a headpiece and, ultimately, to an implanted cochlear stimulator, the sound processor 100b operates in the second mode and transmits audio signals derived from sounds received at the non-implanted ear to the sound processor 100a so that offside sounds can also be processed by the sound processor 100a. Transmitting signals received at one ear to the other ear is sometimes referred to a contralateral routing of signals ("CROS") and, accordingly, the second mode may be referred to as the CROS mode. As a result, the present system provides improved hearing (e.g., improved awareness of contralateral sounds, and improved ability to understand speech in background noise). In at least some implementations, the sound processors 100a and 100b will automatically (i.e., without user input) determine which mode to operate in. As such, the user can obtain improved hearing by simply employing the spare sound processor on the non-implanted side.

Figures 2, 3:
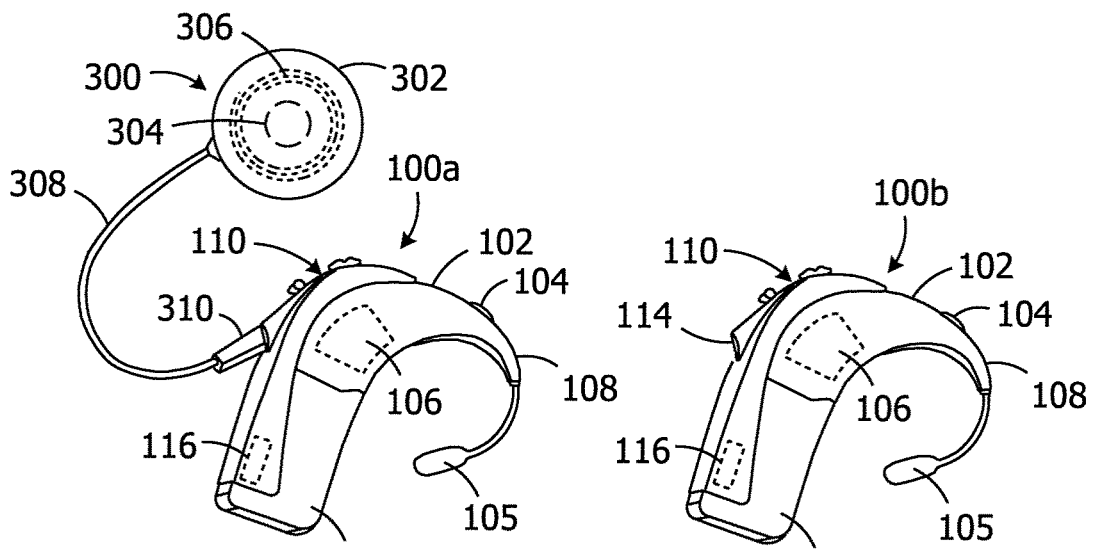
FIG. 2 is a perspective view a sound processor with a headpiece connected thereto.
FIG. 3 is a perspective view a sound processor without a headpiece connected thereto.

Referring to FIGS. 2 and 3, the exemplary BTE sound processors 100a and 100b each include a housing 102, microphones 104 and 105, processor apparatus 106, and a retention member 108. The processor apparatus 106 may include any hardware, non-transitory computer readable media with computer-implemented instructions (e.g., software), firmware, or combinations thereof configured to perform one or more of the processes described herein including, but not limited to, the processes described below with reference to FIGS. 5 and 7. For example, the processor apparatus 106 may include one or more processors, digital signal processors ("DSPs"), filters, programmable memory units, storage mediums. A control panel 110 that is positioned on the exterior of the housing 102 has a volume button and a program selector switch. The sound processors 100a and 100b also include a primary or secondary battery or other power supply (not shown) that supplies power to the processor apparatus 106 and other power consuming components of the sound processors. In the illustrated implementation, the power supply is carried by a removable battery holder 112 that is secured to housing 102. A headpiece port 114 is located adjacent to the control panel 110. The exemplary sound processors also include a transceiver 116 that is used to transmit and receive wireless signals including, but not limited to, wireless audio signals.

There is no on/off button in the illustrated embodiment and the processors 100a and 100b are turned on when the battery holder 112 is attached to the housing 102 and are turned off when the battery holder is removed. An on/off button may be provided in other implementations. Here, the battery holder 112 may continue to be used, or a secondary battery may be permanently housed within the hearing assistance device and the battery holder may be omitted. Such a hearing assistance device may be placed in a battery charger as necessary.

Figure 4:
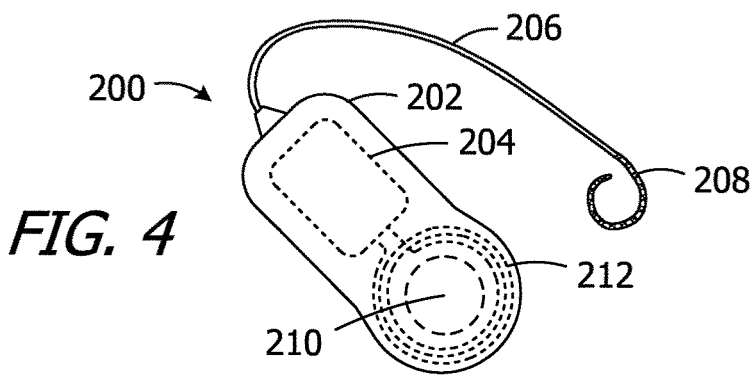
FIG. 4 is a top view of an implantable cochlear stimulator.

As illustrated in FIG. 4, the exemplary cochlear stimulator 200 includes a flexible housing 202 formed from a silicone elastomer or other suitable material, a stimulation processor 204, a cochlear lead 206 with an electrode array 208, and a positioning element (i.e., a magnet or other ferromagnetic material) 210. The cochlear stimulator 200 also includes data and power receiver apparatus which, in the illustrated implementation, consists of an antenna 212 (e.g., a coil antenna) and a receiver (not shown). The stimulation processor 204 and receiver may be located on a common circuit board, or on separate boards. The antenna 212 and receiver receive stimulation data and power from the headpiece 300.

Referring to FIG. 2, the exemplary headpiece 300 includes a housing 302, a positioning magnet 304 that is attracted to the positioning element 210 of the cochlear stimulator 200, a coil antenna 306 (or other suitable antenna) and a transmitter (not shown). The headpiece 300 is connected to the associated sound processor by a cable 308 and a connector 310 that may be inserted into the headpiece port 114. A wireless connection between the headpiece 300 and associated sound processor may be employed in other implementations.

Figure 5:
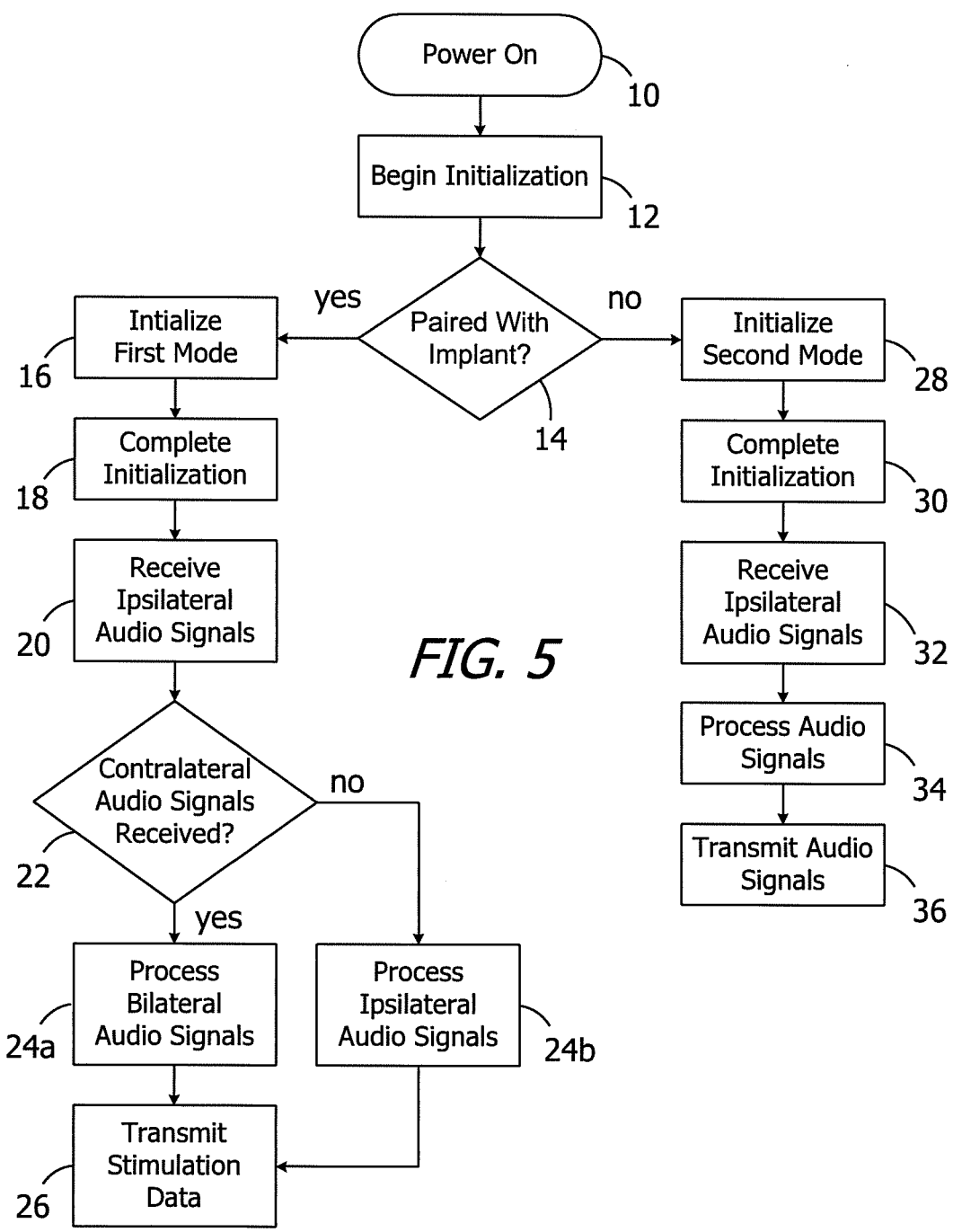
FIG. 5 is flow chart showing a method in accordance with one embodiment of a present invention.

FIG. 5 is a flow chart showing certain aspects of an exemplary sound processor operational method that may be employed in conjunction with the sound processors 100*a* and 100*b* and, accordingly, reference is made to sound processors 100*a* and 100*b* to facilitate understanding of the method. The method is applicable to any other processors that are capable of performing the method.

After a sound processor (e.g., sound processor 100*a* or 100*b*) is powered on (step 10) by, for example, attaching the battery holder 112 to the housing 102 or by pressing an on/off button in other embodiments, the initialization procedure begins (step 12).

As part of the initialization, the sound processor determines whether or not it is paired, i.e., is locked or soon to be locked, with a cochlear implant such as the implanted cochlear stimulator 200 (step 14). This determination may be made in a variety of ways. In one exemplary implementation, the sound processor (e.g., sound processor 100*a* or 100*b*) will transmit power and attempt to communicate with an implanted cochlear stimulator by way of the headpiece 300 when the headpiece is positioned on the head over the cochlear stimulator. The implanted cochlear stimulator 200 receives power from a sound processor on the implanted ear and, in response to the attempted communication, transmits an identification signal to the sound processor 100*a* by way of the headpiece 300. The sound processor 100*a* determines, based on receipt of the identification signal, that it is paired with an implanted cochlear stimulator. Conversely, based on a determination that it is has not received the identification signal, the sound processor 100*a* will determine that it is not paired with an implanted cochlear stimulator.

In those instances where the sound processor 100*a* determines that it is paired with a cochlear implant (step 14), the first mode of operation is initialized (step 16). Here, the processor apparatus 106 of the sound processor 100*a* runs the program associated with the particular cochlear implant that is identified by the identification signal and the overall initialization of the sound processor (e.g., sound processor 100*a*) is completed (step 18). The sound processor 100*a* will then operate as an ipsilateral (or "stimulating") sound processor and will also continue to monitor for communication with the implant. The initialized processor apparatus 106 receives ipsilateral audio signals from its own microphones 104 and/or 105 (step 20) and also detects and receives contralateral audio signals from the microphones 104 and/or 105 of the sound processor (e.g., sound processor 100*b*) on the non-implanted ear (step 22) by way of transceiver 116. The processor apparatus 106 mixes the audio signals from both sides (or "bilateral signals") and converts the mixed audio signals into stimulation data (step 24*a*) that is transmitted to the headpiece 300 (step 26), and is transmitted from the headpiece to the cochlear implant 200.

In some embodiments, the sound processor on the non-implanted ear will transmit one or more command signals (e.g., command signals generated by the processor apparatus 106) to the sound processor on the implanted ear. One exemplary command signal would be a trigger which indicates that bilateral sound processing should be performed with the sound processor on the implanted ear. Alternatively, or in addition, the command signal could specify the relative percentages of the ipsilateral and contralateral audio signals in the audio mix. The default mix command may, for example, be 50% ipsilateral and 50% contralateral. The mix command may be varied (e.g., 75% ipsilateral and 25% contralateral) in those instances where there is a low signal-to-noise ratio on the contralateral side. The sound processors may also be configured such that the mix will be varied in a similar fashion in response to a determination by the sound processor on the implanted side that there is a low signal-to-noise ratio on the ipsilateral side.

It should be noted here that a sound processor will also operate in the first mode, due to its pairing with a cochlear implant, in those instances where no contralateral audio signals are received from a contralateral sound processor (step 24*b*). The lack of contralateral audio signals may occur when, for example, the user simply leaves the second sound processor in storage. The processor apparatus 106 will simply process the audio signals received by the microphones 104 and/or 105 of the associated sound processor (e.g., sound processor 100*a*) and convert those audio signals into stimulation data (step 26).

In those instances where the sound processor determines, in response to a failure to receive an identification signal within a predetermined time period, that it is not paired with a cochlear implant (step 14), the second mode of operation is initialized (step 28) and the overall initialization of the sound processor (e.g., sound processor 100*b*) is completed (step 30). Here, the sound processor 100*b* will run a program that causes it to run as a contralateral (or "transmitting") sound processor. Ipsilateral audio signals are received by the microphones 104 and/or 105 (step 32) of the initialized sound processor associated with the non-implanted ear (e.g., sound processor 100*b*) and are processed (step 34). The processed signals are transmitted by the transceiver 116 (step 36) to the sound processor associated with the implanted ear (e.g., sound processor 100*a*). A sound processor in the second mode will also continue to monitor for an identification signal from a cochlear implant. As such, should there be a delay that exceeds the predetermined period prior to the user positioning the headpiece over the cochlear implant and establishing communication with the cochlear implant, the sound processor will switch from the second mode to the first mode.

Figure 6:
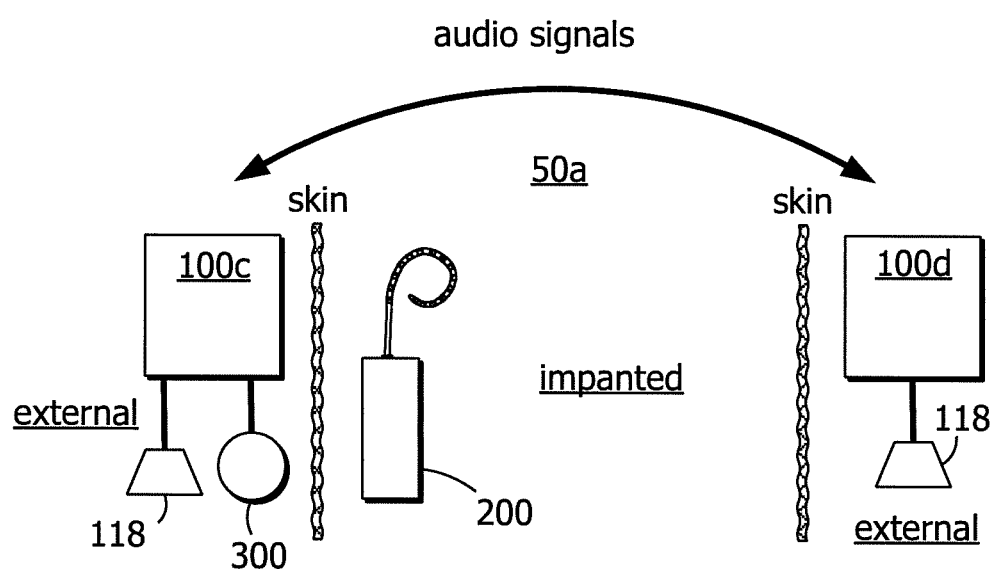
FIG. 6 is a block diagram of an ICS system in accordance with one embodiment of a present invention.

The present inventions are also applicable to electro-acoustic stimulation ("EAS") systems. Such systems are useful when the patient has retained some hearing in one or both ears. The exemplary system 50*a* illustrated in FIG. 6 is essentially identical to the system 50 described above with reference to FIGS. 1-5 and similar elements are represented by similar reference numerals. For example, the sound processors 100*c* and 100*d* are essentially identical in structure and function to sound processors 100*a* and 100*b*. Here, however, each of the sound processors 100*c* and 100*d* also includes a receiver (or "speaker") 118. The speaker 118 may be integrated into the sound processor, e.g., replacing the microphone 105 (FIGS. 2 and 3), or connected to the sound processor by way of a cable and plug in a manner similar to a conventional earphone. With respect to the implanted side, the system provides cochlear implant and hearing aid functionality to the same ear. The receiver 118 delivers amplified low frequency sound pressure waves to the ear canal, and the cochlear implant 200 stimulates the high frequencies in response to stimulation data received from the sound processor (e.g. sound processor 100*c*) by way of the headpiece 300. The auditory nerve combines the acoustic and electrical stimuli into one auditory signal. On the non-implanted side, the sound processor will transmit audio signals to the ear canal by way of the receiver 118. In some instances, and depending on the particular user, the sound processor 100*c* will receive contralateral audio signals from sound processor 100*d*, and the sound processor 100*d* will receive contralateral audio signals from sound processor 100*c*, by way of transceivers 116. Such transmission of off-side signals in combination with an EAS system, where the ear is stimulated both electrically and acoustically, may be referred to as the system's BiCROS mode.

Figure 7:
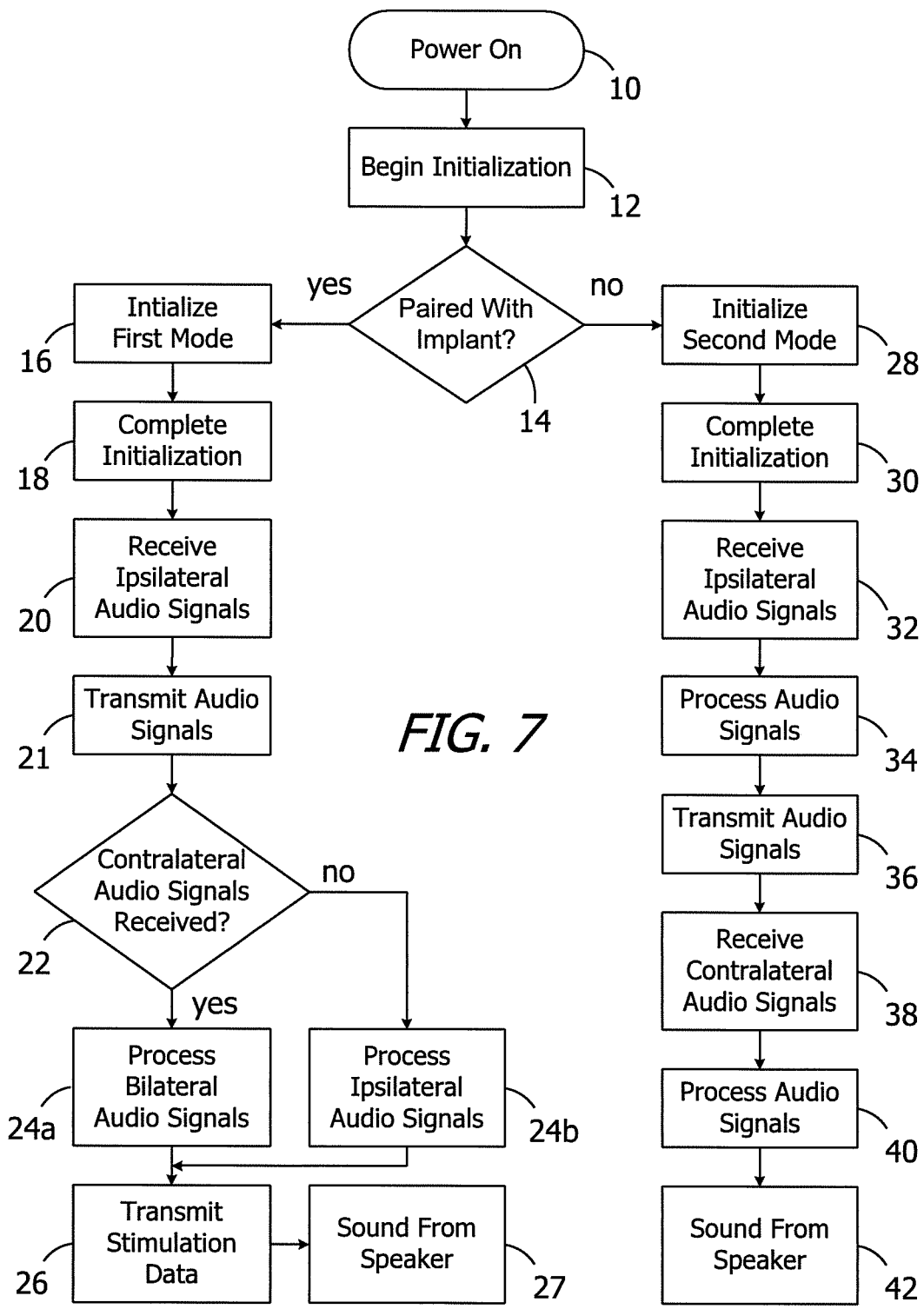
FIG. 7 is flow chart showing a method in accordance with one embodiment of a present invention.

As illustrated for example in FIG. 7, the method associated with system 50*a* is substantially similar to the method illustrated in FIG. 5 and similar steps are represented by similar reference numerals. Here, however, the sound processor on the implanted side (e.g., sound processor 100*c*) will in at least some instances transmit the audio signals from its own microphones 104 and/or 105 (step 21) to the sound processor on the non-implanted side (e.g., sound processor 100*d*). The sound processor on the implanted side (e.g., sound processor 100*c*) will also process the audio signals from the implanted and non-implanted sides (step 24) and, in addition transmitting stimulation data to the headpiece 300 (step 26), the sound processor will provide audio signals to the receiver 118 so that sound may be delivered to the ear canal of the implanted ear (step 27). For example, low frequency sounds may be provided to the ear canal by the receiver 118 while the cochlear implant 200 stimulates the high frequencies. On the non-implanted side, and in addition to processing audio signals (step 34) and transmitting the processed audio signals to the implanted side (step 36), the sound processor (e.g., sound processor 100*d*) will receive contralateral audio signals from the implanted side (step 38). These audio signals may be processed (step 40) and sound, that is a combination of ipsilateral and contralateral sound, may be transmitted to the ear canal of the non-implanted ear by way of the receiver 118 (step 42).

It should also be noted that, in various instances and depending on the particular user, steps 27 and/or 38-42 may be omitted. For example, in those instances where the user is profoundly deaf in the non-implanted ear, the sound processors 100*c* and 100*d* may be configured so as to not supply sound to the ear canal when not paired with an implant.

The exemplary systems 50 and 50*a* may also be configured to provide other bilateral functionality to cochlear implant users with a unilateral implantation. For example, the systems may be configured to suppress ambient noise, i.e., speech or other sound from non-target sound sources ("non-target sources"), while preserving sound from the target sound source ("target source"). Beamforming is a directional microphone technique that involves two or more microphones and can be used to preserve sound from the target source while filtering out or otherwise attenuating sound from non-target sources. The sound processors 100*a* and 100*b* (and sound processors 100*c* and 100*d*), which each include a pair of microphones 104/105, may be configured to interactively exchange data between one another to provide binaural beamforming functionality, such as that associated with the Phonak StereoZoom system.

Although the inventions disclosed herein have been described in terms of the preferred embodiments above, numerous modifications and/or additions to the above-described preferred embodiments would be readily apparent to one skilled in the art. By way of example, but not limitation, the present inventions are applicable to body worn sound processors as well as systems that include one body worn sound processor and one BTE sound processor. The present inventions are also applicable to sound processor that communicate directly with the implantable cochlear stimulator by way of an internal antenna (i.e., without a headpiece) and sound processors wherein the sound processing and headpiece functionalities are incorporated into a single structure (see, e.g., U.S. Pat. Nos. 8,515,112 and 8,811,643, which are incorporated herein by reference). The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A system for use with a cochlear implant and a headpiece, the system comprising:
   a microphone;
   a transmitter configured to transmit audio signals to a contralateral sound processor; and
   processor apparatus operably connected to the microphone and configured to operate in a first mode, in response to a detection of the cochlear implant, to convert audio signals from the microphone into stimulation data and to transfer the stimulation data to the cochlear implant by way of the headpiece, and to operate in a second mode, in response to a failure by the processor apparatus to detect the cochlear implant, to transfer the audio signals to a contralateral sound processor with the transmitter.

2. A system as claimed in claim 1, wherein
   the processor apparatus detects the cochlear implant by detecting an identification signal from the cochlear implant.

3. A system as claimed in claim 1, wherein the transmitter is configured to wirelessly transmit audio signals to the contralateral sound processor.

4. A system as claimed in claim 1, further comprising:
   a speaker operably connected to the processor apparatus;
   wherein, when operable in the second mode, the processor apparatus also transfers an amplified sound signal to the speaker.

5. A system as claimed in claim 1, wherein
   the processor apparatus performs an initialization procedure when the system transitions from an off state to an on state; and
   the processor apparatus attempts to detect the cochlear implant during the initialization procedure.

6. A system as claimed in claim 1, wherein
   the processor apparatus, when in the first mode, converts audio signals from the microphone and from the contralateral sound processor into stimulation data.

7. A system as claimed in claim 1, wherein
   the processor apparatus generates a command signal that is transmitted to the contralateral sound processor when operating in the second mode.

8. A cochlear implant system, comprising:
   a single cochlear implant;
   a first sound processor with a first microphone;
   a second sound processor with a second microphone;

wherein the first sound processor is configured to determine whether or not it is paired with the single cochlear implant, to convert audio signals from the first microphone into stimulation data in response to being paired with the single cochlear implant, and to transfer the audio signals from the first microphone to the second sound processor in response to not being paired with the single cochlear implant; and wherein the second sound processor is configured to determine whether or not it is paired with the single cochlear implant, to convert audio signals from the second microphone into stimulation data in response to being paired with the single cochlear implant, and to transfer the audio signals from the second microphone to the first sound processor in response to not being paired with the single cochlear implant.

9. A cochlear implant system as claimed in claim 8, wherein the single cochlear implant transmits an identification signal;

the first sound processor is configured to determine whether or not it has received the identification signal; and the second sound processor is configured to determine whether or not it is has received the identification signal.

10. A cochlear implant system as claimed in claim 8, wherein the first sound processor automatically determines whether or not it is paired with the single cochlear implant during initialization of the first sound processor; and the second sound processor automatically determines whether or not it is paired with the single cochlear implant during initialization of the second sound processor.

11. A cochlear implant system as claimed in claim 8, wherein the first sound processor includes a first speaker and is configured to deliver sound to an ear canal with the first speaker in response to being paired with the single cochlear implant; and the second sound processor includes a second speaker and is configured to deliver sound to an ear canal with the second speaker in response to being paired with the single cochlear implant.

12. A cochlear implant system as claimed in claim 8, wherein the first sound processor is configured to transfer a command signal to the second sound processor in response to not being paired with the single cochlear implant; and the second sound processor is configured to transfer a command signal to the first sound processor in response to not being paired with the single cochlear implant.

* * * * *